(12) United States Patent
Nagano et al.

(10) Patent No.: US 8,465,985 B2
(45) Date of Patent: Jun. 18, 2013

(54) FLUORESCENT PROBE

(75) Inventors: Tetsuo Nagano, Tokyo (JP); Hirotatsu Kojima, Tokyo (JP); Sakiko Aizawa, Tokyo (JP); Kazuki Kiyose, Tokyo (JP)

(73) Assignee: The University of Tokyo, Tokyo (JP)

( * ) Notice: Subject to any disclaimer, the term of this patent is extended or adjusted under 35 U.S.C. 154(b) by 442 days.

(21) Appl. No.: 12/527,898

(22) PCT Filed: Feb. 29, 2008

(86) PCT No.: PCT/JP2008/000392
§ 371 (c)(1),
(2), (4) Date: Feb. 2, 2011

(87) PCT Pub. No.: WO2008/108074
PCT Pub. Date: Sep. 12, 2008

(65) Prior Publication Data
US 2011/0117666 A1 May 19, 2011

(30) Foreign Application Priority Data

Mar. 1, 2007 (JP) .................................. 2007-050941

(51) Int. Cl.
*G01N 21/76* (2006.01)
(52) U.S. Cl.
USPC ............... 436/172; 436/81; 436/92; 548/259; 548/455
(58) Field of Classification Search
None
See application file for complete search history.

(56) References Cited

U.S. PATENT DOCUMENTS

| | | |
|---|---|---|
| 6,903,226 B2 | 6/2005 | Nagano et al. |
| 7,074,823 B2 | 7/2006 | Nagano et al. |

(Continued)

FOREIGN PATENT DOCUMENTS

| | | |
|---|---|---|
| EP | 1394219 | 3/2004 |
| JP | 2000-239272 | 9/2000 |

(Continued)

OTHER PUBLICATIONS

International Report on Patentability issued in connection with International Application No. PCT/JP2008/000392, dated Sep. 11, 2009. (English and Japanese.).

(Continued)

*Primary Examiner* — Robert Xu
(74) *Attorney, Agent, or Firm* — Greenblum & Bernstein, P.L.C.

(57) ABSTRACT

A fluorescent probe comprising a compound represented as (Fluorophore A)-S-(Fluorophore B) (Fluorophore A and Fluorophore B are fluorophores which emit fluorescence when they are irradiated with an excitation light of a wavelength of 600 to 950 nm, Fluorophore A has a property that it shows change of fluorescence characteristic before and after a specific reaction with a substance to be measured, and S represents a spacer which connects Fluorophore A and Fluorophore B), which compound shows substantial change in efficiency of fluorescence resonance energy transfer between Fluorophore A and Fluorophore B before and after the specific reaction with the objective substance, wherein Fluorophore A is represented by the following formula (AI):

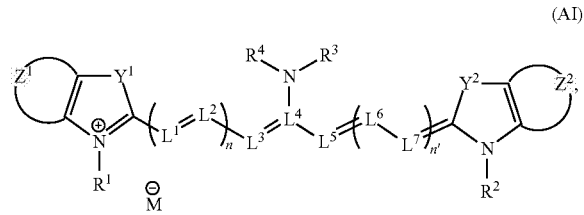

which uses and shows an excitation light wavelength/fluorescence wavelength in the near infrared region, lights of which region show superior biological tissue permeability, and enables measurement of a substance to be measured by the ratio method.

7 Claims, 1 Drawing Sheet

U.S. PATENT DOCUMENTS

| | | | |
|---|---|---|---|
| RE40,572 | E | 11/2008 | Nagano et al. |
| 2004/0235902 | A1 | 11/2004 | Nagano et al. |
| 2005/0037332 | A1 | 2/2005 | Komatsu et al. |
| 2007/0298507 | A1 | 12/2007 | Nagano et al. |
| 2008/0261314 | A1 | 10/2008 | Nagano et al. |
| 2009/0258434 | A1 | 10/2009 | Nagano et al. |

FOREIGN PATENT DOCUMENTS

| | | |
|---|---|---|
| JP | 2000-316598 | 11/2000 |
| JP | 2003-501540 | 1/2003 |
| JP | 2004-315501 | 11/2004 |
| WO | 00/75237 | 12/2000 |
| WO | 01/62755 | 8/2001 |
| WO | 02/102795 | 12/2002 |
| WO | 2005/080331 | 9/2005 |

OTHER PUBLICATIONS

K. Kiyose et al., "Development of a Ratiometric Fluorescent Zinc Ion Probe in Near-Infrared Region, Based on Tricarbocyanine Chromophore", J. Am. Chem. Soc., vol. 128, No. 20, pp. 6548-6549, 2006.

E. Sasaki et al., "Highly Sensitive Near-Infrared Fluorescent Probes for Nitric Oxide and Their Application to Isolated Organs", J. Am. Chem. Soc., vol. 127, No. 11, pp. 3684-3685, 2005.

H. Kojima et al., "Development of Near-Infrared Fluorescent Probes for Nitric Oxide and Zinc Ion", Proc. of SPIE. Int. Soc. Opt. Eng., vol. 6441, pp. 64411P.1-64411P.12, 2007.

K. Kiyose et al., "Tricarbocyanine . . . Kaihatsu.", Dai 126 Kai the Pharmaceutical Society of Japan SENDAI 2006 Yoshishu 2, , vol. 126, No. 2, p. 5, 030-130, Mar. 6, 2006.

U.S. Appl. No. 12/526,677, filed Aug. 11, 2009.

U.S. Appl. No. 12/447,723, filed Apr. 29, 2009.

U.S. Appl. No. 12/527,793, filed Aug. 19, 2009.

English and Japanese version of International Search Report for International Application No. PCT/JP2008/000392.

Reyes et al., "A fluorescence method to determine picomole amounts of Zn(II) in biological systems", Biol. Res., 27, 1994, pp. 49-56.

Tsuda et al., "Expression of Zinc Transporter Gene, ZnT-1, Is Induced after Transient Forebrain Ischemia in the Gerbil", The Journal of Neuroscience., 17(17), Sep. 1, 1997, pp. 6678-6684.

Koike et al., "A Novel Biomimetic Zinc(II)—Fluorophore, Dansylamidoethyl-Pendant Macrocyclic Tetraamine 1.4,7,10-Tetraazacyclododecane (Cyclen)", J. Am. Chem. Soc., 1996, 118, pp. 12696-12703.

The catalogue of Molecular Probe (Handbook of Fluorescent Probes and Research Chemicals, Tenth Edition), "19.7 Fluorescent indicators for Zn2+ and Other Metal Ions",), Chapter 19 , pp. 913-924.

Kawanishi et al., Angew. Chem. Int. Ed., 39(19) , 2000, pp. 3438-3440.

Ozmen et al., "Infrared fluorescence sensing of submicromolar calcium: pushing the limits of photoinduced electron transfer", Tetrahedron Lett., 41(2000), pp. 9185-9188.

Mason W.T., "Chapter Eight Fluorescent Probes in Practice—Potential Artifacts", in Fluorescent and Luminescent Probes for Biological Activity, Second Edition, Edited by Mason W.T., Academic Press, 1999, pp. 108-113, 160-179.

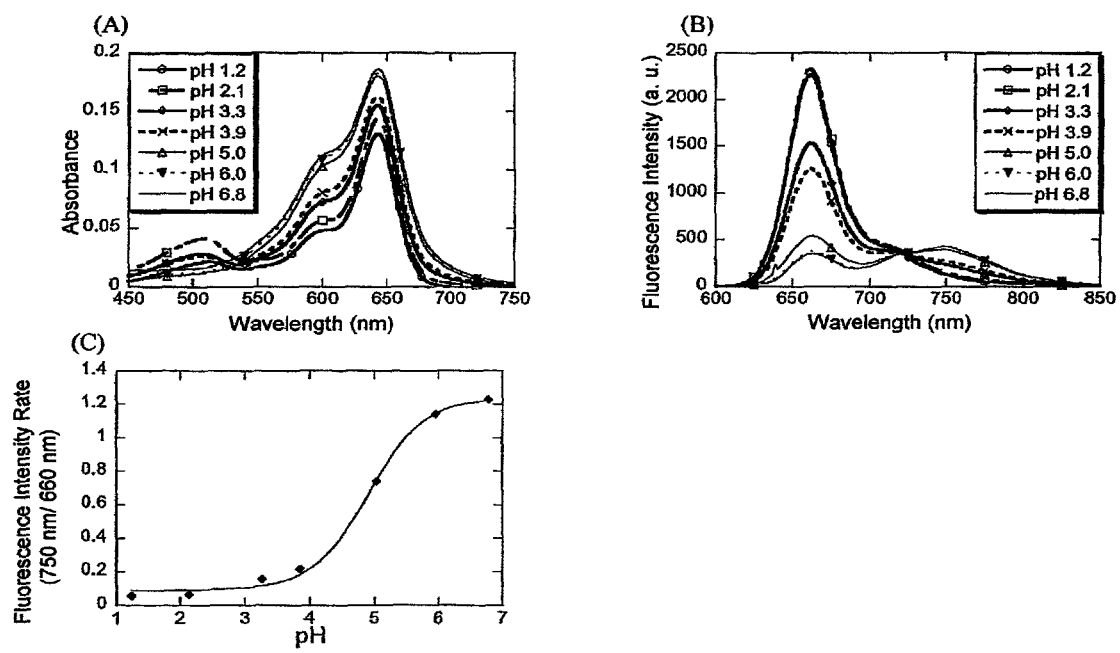

US 8,465,985 B2

FLUORESCENT PROBE

TECHNICAL FIELD

The present invention relates to a fluorescent probe. More specifically, the present invention relates to a fluorescent probe utilizing fluorescence resonance energy transfer for which an excitation light/fluorescence of the near infrared region is usable.

BACKGROUND ART

Fluorescent probes for imaging biological phenomena have been actively developed in researches of life chemistry in recent years, and various fluorescent probes for measurement of pH, various metal ions, active oxygen species, and the like have been proposed. For example, as fluorescent probes for measuring pH, there have been proposed BCECF (2',7'-bis(carboxyethyl)-4 or 5-carboxyfluorescein) and derivatives thereof, CFDA (carboxyfluorescein diacetate) and derivatives thereof, SNARF-1(seminaphthorhodafluor) and derivatives thereof [the catalogue of Molecular Probe (Handbook of Fluorescent Probes and Research Chemicals, Tenth Edition), Chapter 20(pH indicators), for all the compounds]. Further, as fluorescent probes for measuring zinc ion, there have been proposed TSQ (Reyes, J.G., et al., Biol. Res., 27, 49, 1994), zinquin ethyl ester (Tsuda, M., et al., J. Neurosci., 17, 6678, 1997), dansylaminoethylcyclen (Koike, T., et al., J. Am. Chem. Soc., 118, 12696, 1996), and Newport Green [the catalogue of Molecular Probe (Handbook of Fluorescent Probes and Research Chemicals, Tenth Edition), Chapter 19(Calcium ion, magnesium ion, zinc ion and other metal ions)], and further, there have been proposed, by the inventors of the present invention, a zinc ion probe comprising fluorescein as a fluorescent mother nucleus (Japanese Patent Laid-open Publication (KOKAI) No. 2000-239272, International Patent Publication WO01/062755, Japanese Patent Laid-open Publication No. 2004-315501), an zinc ion probe comprising benzofuran as a fluorescent mother nucleus (International Patent Publication WO02/102795), and the like.

Although fluorescent characteristics of these fluorescent probes desirably change only when they react with a target measurement object, they are often influenced by other factors. In particular, application of fluorescent probes to cells or biological tissues has a problem that it involves many factors which affect the measurement. For example, concentration of a fluorescent probe introduced into cells may vary depending on type of the cells, intensity of excitation light may vary in measurement regions depending on thickness of cell membrane, a fluorescent probe may localize at a highly hydrophobic portion such as membranes, and the like.

As a method for reducing measurement errors induced by these factors to realize accurate quantitative analysis, the ratio method has been developed and used (Kawanishi Y., et al, Angew. Chem. Int. Ed., 39(19), 3438, 2000). This method comprises the step of measuring fluorescence intensities at two different wavelengths in a fluorescence spectrum or an excitation spectrum to detect a ratio thereof. In this method, influence of concentration of the fluorescent probe itself or intensity of excitation light can be ignored, and measurement errors can be eliminated, which may be caused by localization of the fluorescent probe itself, change of concentration thereof, discoloration thereof, or the like, when the measurement is performed at one wavelength. In order to enable the above ratio measurement, there is needed a fluorescent probe which shows change in excitation light wavelength or fluorescence wavelength before and after a reaction with a measurement object. For example, the pH fluorescent probe SNARF-1 has a property that the peak of fluorescence wavelength shifts to the longer wavelength side due to deprotonation when pH shifts to the alkaline side, and when it is excited around 500 nm, fluorescence intensity around 580 nm decreases with increase of pH, whilst fluorescence intensity around 640 nm increases with increase of pH. Therefore, if a solution containing this compound is irradiated with an excitation light, and ratio of fluorescence intensities measured at that time at appropriate two wavelengths is obtained, pH can be accurately measured regardless of probe concentration, intensity of light source, size of cells, and the like. Further, the zinc ion fluorescent probe described in International Patent Publication WO02/102795 is a fluorescent probe based on the principle of intramolecular charge transfer, and uses or shows an excitation wavelength of 354 nm and a fluorescence wavelength of 532 nm when it does not capture zinc ion, but shows about 20 nm blue shift of the peak in the excitation spectrum depending on concentration of zinc ions. Therefore, by using wavelengths of 335 nm and 354 nm as the excitation wavelengths, measuring fluorescence intensities at those excitation wavelengths, and obtaining the ratio of the intensities, zinc ion concentration can be accurately measured irrespective of the probe concentration, light source intensity, size of cells, and the like. However, a problem arises that they are ratio type fluorescent probes utilizing or showing excitation light wavelength/fluorescence wavelength of the visible light region or shorter, and such excitation light shows poor permeability into biological tissues. Furthermore, they fail to solve the problem that measurement is easily influenced by autofluorescence of cells themselves.

Cyanine dyes are widely used in various fields, and they are also used in the field of fluorescence imaging for studying physiological functions as fluorescence labels of biological molecules. Among these cyanine dyes, tricarbocyanine type dyes are fluorescent dyes showing a maximum absorption wavelength and maximum fluorescence wavelength in the near infrared region of around 650 to 950 nm, of which lights are comparatively less absorbed by biological molecules, and thus they have an advantage that they allow use of lights of a wavelength which can penetrate into deep parts of biological tissues. In addition, since biological substances scarcely emit autofluorescence of the near infrared region, the characteristics of tricarbocyanine type dyes are suitable for in vivo imaging.

In addition to cyanine type dyes for directly labeling biological molecules with fluorescence, tricarbocyanine dyes which specifically react with biological molecules to change fluorescence intensity thereof have recently been developed. Examples include a near infrared fluorescent probe for calcium ions (Ozmen, B., et al., Tetrahedron Lett., 41, pp. 9185-9188, 2000), and a near infrared fluorescent probe for nitrogen monoxide (NO) (WO2005/080331). These fluorescent probes are probes showing only fluorescence intensity changes, which do not show changes of excitation wavelength and fluorescence wavelength, before and after a specific reaction with a biological molecule. Moreover, as pH probes, there are the compounds described in International Patent Publication WO00/75237 and CypHer (GE Healthcare Bioscience). They show increase of fluorescence intensity with decrease of pH in the neutral region or lower pH region on the basis of the principle that the nitrogen atom of the nitrogen-containing hetero aromatic ring bonded to the polymethine chain of the cyanine structure is protonated to emit fluorescence. Furthermore, the inventors of the present invention recently developed a near-infrared fluorescent probe for zinc ion (Japanese Patent Application No. 2005-057265) and a near-infrared fluorescent probe used for pH measurement (Japanese Patent Application No. 2007-035768). These are ratio fluorescent probes of which excitation wavelength changes depending on changes of pH or concentration of zinc ion. They show a maximum absorption wavelength of 650 to 800 nm, which wavelength shows superior permeability into biological tissues, and a marked wavelength shift in the peak of excitation spectrum according to change of zinc ion concentration or pH, therefore, by irradiating them with excitation lights of appropriate two wavelengths of 650 to 800 nm, and obtaining ratio of fluorescence intensities measured at the wavelengths, zinc ion concentration and pH in a deep part of biological tissue can be highly accurately measured.

Further, since fluorescence change by fluorescence resonance energy transfer (FRET) may also be change of two wavelength ratio type, the ratio measurement is also possible with a FRET type fluorescent probe, which makes it possible to quantitatively measure a measurement object irrespective of probe concentration, light source intensity, size of cells, and the like. However, most of conventionally known fluorescent probes utilizing FRET (for example, the fluorescent probe described in Japanese Patent Laid-open Publication No. 2000-316598 and the like) utilize fluorescence of the visible region, and almost no fluorescent probes utilizing or showing an excitation light wavelength/fluorescence wavelength of the near infrared region are known, except an FRET type pH probe described in International Patent Publication WO00/075237 which utilizes on/off of fluorescence in connection with pH change. This probe described in International Patent Publication WO00/075237 has a problem that it can be used only as a pH probe, and it cannot be applied to a probe for an substance to be measured such as other metal ions and enzyme substrates.

DISCLOSURE OF THE INVENTION

Object To Be Achieved By the Invention

An object of the present invention is to provide a fluorescent probe using and showing an excitation light wavelength/fluorescence wavelength in the near infrared region, lights of which region show superior biological tissue permeability, which probe enables measurement of an objective substance by the ratio method. Another object of the present invention is, in particular, to provide a pH fluorescent probe containing a compound having the aforementioned characteristics and a method for measuring pH using the pH fluorescent probe, as well as a zinc ion fluorescent probe and a method for measurement of zinc ion using such a zinc ion fluorescent probe.

Means For Achieving the Object

The inventors of the present invention conducted various researches in order to achieve the objects mentioned above, and as a result, found that, by using a fluorescent probe obtained by connecting a specific fluorescent compound (referred to as "Fluorophore A" later) which uses and shows an excitation wavelength/fluorescence wavelength of the near infrared region, and specifically reacts with an substance to be measured in a sample to show marked change of the excitation light wavelength, and a compound (referred to as "Fluorophore B" later) which itself emits fluorescence of the near infrared region, and functions as a donor or receptor showing a FRET relationship with respect to the specific fluorescent compound, the reaction of the fluorescent probe and the substance to be measured was successfully measured as change of FRET efficiency of the fluorescent probe using fluorescence. The inventors of the present invention also found that an substance to be measured in a sample can be measured by the ratio method according to the aforementioned method by using excitation wavelength/fluorescence wavelength of the near infrared region, lights of which region show superior biological tissue permeability, and that an substance to be measured in a deep part of a biological tissue was successfully measured highly accurately without being influenced by environmental difference of biological tissues, autofluorescence originating in endogenous substances in biological tissues and the like. The present invention was accomplished on the basis of these findings.

The present invention thus provides a fluorescent probe comprising a compound represented by the following general formula (I):

(Fluorophore A)-S-(Fluorophore B)  (I)

(wherein Fluorophore A and Fluorophore B are fluorophores which emit fluorescence when they are irradiated with an excitation light of a wavelength of 600 to 950 nm, Fluorophore A has a property that it shows change of fluorescence characteristic before and after a specific reaction with an substance to be measured, and S represents a spacer which connects Fluorophore A and Fluorophore B), which compound shows substantial change in efficiency of fluorescence resonance energy transfer between Fluorophore A and Fluorophore B before and after the specific reaction with the substance to be measured, wherein Fluorophore A is represented by the following formula (AI):

[Formula 1]

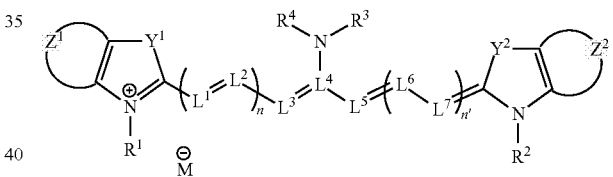

(AI)

[wherein $R^1$ and $R^2$ independently represent a $C_{1-18}$ alkyl group which may have a substituent; $R^3$ and $R^4$ independently represent hydrogen atom, or a substituent for detecting the substance to be measured, provided that $R^3$ and $R^4$ do not simultaneously represent hydrogen atom, and $R^3$ and $R^4$ may bind to each other to form a ring structure for detecting the substance to be measured; $Y^1$ and $Y^2$ independently represent —O—, —S—, —Se—, —CH=CH—, —C($R^5$)($R^6$)—, or —N($R^7$)— (wherein $R^5$, $R^6$ and $R^7$ independently represent hydrogen atom, or a $C_{1-6}$ alkyl group which may have a substituent); n and n' independently represent 0, 1 or 2; $Z^1$ and $Z^2$ independently represent a nonmetallic atom group required to form a benzo-condensed ring which may have a substituent or a naphtho-condensed ring which may have a substituent; $L^1$, $L^2$, $L^3$, $L^4$, $L^5$, $L^6$ and $L^7$ independently represent a substituted or unsubstituted methine group, provided that when n or n' is 2, each two of $L^1$ and $L^2$, or each two of $L^6$ and $L^7$ may be the same or different; $M^-$ represents a counter ion in a number required for neutralizing electrical charge, and the combination of $R^3$ and $R^4$ is a combination that provides change in the maximum excitation wavelength of Fluorophore A represented by the formula (AI) before and after detection of the substance to be measured].

According to a preferred embodiment of the aforementioned invention, there is provided the fluorescent probe, wherein Fluorophore A in the aforementioned general formula (I) is represented by the following formula (AII):

[Formula 2]

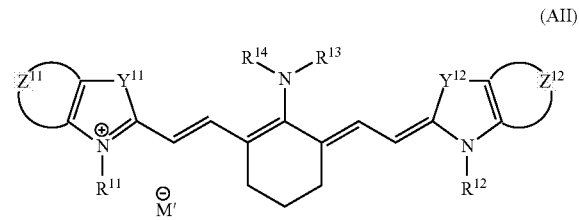

(AII)

[wherein $R^{11}$ and $R^{12}$ independently represent a $C_{1-18}$ alkyl group which may have a substituent; $R^{13}$ and $R^{14}$ independently represent hydrogen atom, or a substituent for detecting the substance to be measured, provided that $R^{13}$ and $R^{14}$ do not simultaneously represent hydrogen atom, and $R^{13}$ and $R^{14}$ may bind to each other to form a ring structure for detecting the substance to be measured; $Y^{11}$ and $Y^{12}$ independently represent —O—, —S—, —Se—, —CH=CH—, —C($R^{15}$)($R^{16}$)—, or —N($R^{17}$)— (wherein $R^{15}$, $R^{16}$ and $R^{17}$ independently represent hydrogen atom, or a $C_{1-6}$ alkyl group which may have a substituent); $Z^{11}$ and $Z^{12}$ independently represent a nonmetallic atom group required to form a benzo-condensed ring which may have a substituent or a naphtho-condensed ring which may have a substituent; $M'^-$ represents a counter ion in a number required for neutralizing electrical charge; and the combination of $R^{13}$ and $R^{14}$ is a combination that provides change in the maximum excitation wavelength of Fluorophore A represented by the formula (AII) before and after detection of the substance to be measured].

According to more preferred embodiments of the aforementioned invention, there are provided the aforementioned fluorescent probe, wherein the substance to be measured is proton, a metal ion, an active oxygen species, an enzymatic reaction substrate, or an enzymatic reaction product; the aforementioned fluorescent probe, wherein Fluorophore B is a tetramethylindodicarbocyanine derivative, and Fluorophore A is represented by the aforementioned formula (AII); the aforementioned fluorescent probe, wherein the metal ion is an alkali metal ion, calcium ion, magnesium ion, or zinc ion; the aforementioned fluorescent probe, wherein the active oxygen species is selected from the group consisting of nitric oxide, hydroxy radical, singlet oxygen, hydrogen peroxide, peroxynitrite, hypochlorite ion, and superoxide; and the aforementioned fluorescent probe, wherein the enzyme is selected from the group consisting of a reductase, an oxidase, and a hydrolase.

According to other preferred embodiments, there are provided the aforementioned fluorescent probe which is used for pH measurement; the aforementioned fluorescent probe, wherein the probe is used for pH measurement, and Fluorophore A is represented by the aforementioned formula (AI) (wherein $R^1$ and $R^2$ independently represent methyl group or 4-sulfobutyl group; one of $R^3$ and $R^4$ is hydrogen atom, and the other is a $C_{1-18}$ alkyl which may have a substituent; $Y^1$ and $Y^2$ represent —C(CH$_3$)$_2$—; both n and n' represent 1; both $Z^1$ and $Z^2$ represent unsubstituted benzo-condensed ring; $L^1$, $L^2$, $L^3$, $L^4$, $L^5$, $L^6$ and $L^7$ represent unsubstituted methine group; and $M^-$ represents a counter ion in a number required for neutralizing electrical charge); and the aforementioned fluorescent probe, wherein Fluorophore A is represented by the aforementioned formula (AI) (wherein $R^1$ and $R^2$ independently represent methyl group or 4-sulfobutyl group; $R^3$ and $R^4$ independently represent a $C_{1-18}$ alkyl group which may have a substituent, an aryl group which may have a substituent, or —(CH$_2$)$_m$—N($R^{21}$)($R^{22}$), one of $R^3$ or $R^4$ is —(CH$_2$)$_m$—N($R^{21}$)($R^{22}$) ($R^{21}$ and $R^{22}$ independently represent a $C_{1-6}$ alkyl group which may have a substituent, or an aryl group which may have a substituent, or $R^{21}$ or $R^{22}$ binds to $R^3$ or $R^4$, respectively, to represent a $C_{1-3}$ alkylene group which may have a substituent, and m represents 1 or 2); $Y^1$ and $Y^2$ represent —C(CH$_3$)$_2$—; both n and n' represent 1, $Z^1$ and $Z^2$ represent an unsubstituted benzo-condensed ring, and $L^1$, $L^2$, $L^3$, $L^4$, $L^5$, $L^6$ and $L^7$ represent unsubstituted methine group; and $M^-$ represents a counter ion in a number required for neutralizing electrical charge).

As the fluorescent probe for measurement of pH, the fluorescent probe containing the following compound is particularly preferred.

[Formula 3]

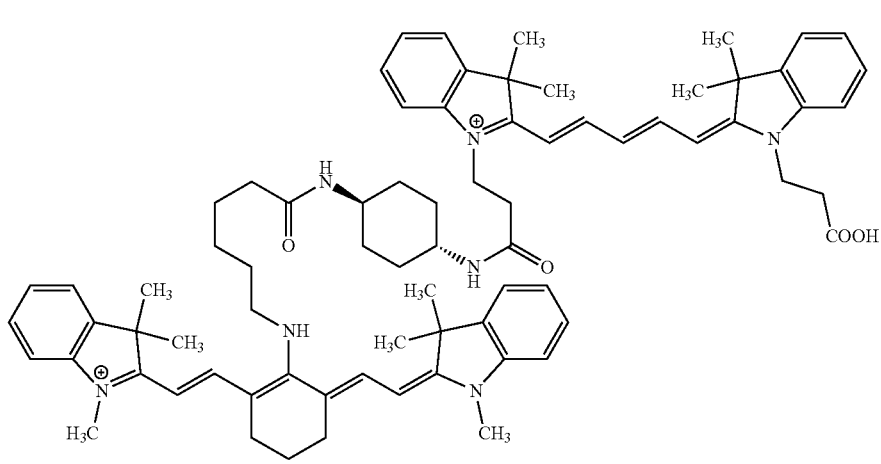

From another aspect, the present invention provides a fluorescent probe for measurement of zinc ion containing a compound represented by the aforementioned general formula (I), wherein Fluorophore A is represented by the aforementioned formula (AI) [wherein $R^1$ and $R^2$ independently represent methyl group or 4-sulfobutyl group; $R^3$ and $R^4$ independently represent hydrogen atom, or a group represented by the following formula (D):

[Formula 4]

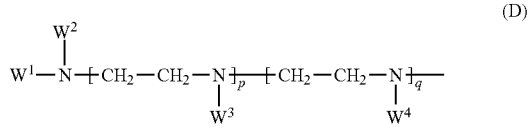

(D)

(wherein $W^1$, $W^2$, $W^3$ and $W^4$ independently represent hydrogen atom, 2-pyridylmethyl group, 2-pyridylethyl group, 2-methyl-6-pyridylmethyl group, or 2-methyl-6-pyridylethyl group, provided that at least one of groups selected from the group consisting of $W^1$, $W^2$, $W^3$, and $W^4$ represents 2-pyridylmethyl group, 2-pyridylethyl group, 2-methyl-6-pyridylmethyl group, and 2-methyl-6-pyridylethyl group; and p and q independently represent 0 or 1) (provided that both $R^3$ and $R^4$ do not simultaneously represent hydrogen atom); $Y^1$ and $Y^2$ represent —$C(CH_3)_2$—; both n and n' represent 1; $Z^1$ and $Z^2$ represent an unsubstituted benzo-condensed ring; $L^1$, $L^2$, $L^3$, $L^4$, $L^5$, $L^6$ and $L^7$ represent unsubstituted methine group; and $M^-$ represents a counter ion in a number required for neutralizing electrical charge)].

From another aspect, the present invention provides a method of using a compound represented by the aforementioned general formula (I); preferably a method using a compound represented by the aforementioned general formula (I) as a fluorescent probe for measurement of an substance to be measured, more preferably as a pH fluorescent probe or a zinc ion fluorescent probe; use of a compound represented by the aforementioned general formula (I) for manufacture of the aforementioned fluorescent probe; and a method for fluorometry of an substance to be measured, which comprises the following steps: (a) contacting a compound represented by the aforementioned general formula (I) and an substance to be measured, and (b) measuring fluorescence intensity of the compound represented by the aforementioned general formula (I) after contacting of the aforementioned step (a) to detect change of FRET efficiency originating from the contacting with the substance to be measured.

From another aspect, the present invention also provides a method for preparing a fluorescent probe containing a compound represented by the aforementioned formula (I), which comprises the step of connecting Fluorophore A represented by the aforementioned formula (AI) which specifically reacts with an substance to be measured in a sample to show change of fluorescent characteristic, and Fluorophore B which serves as a donor or receptor that can induce fluorescence resonance energy transfer with Fluorophores A, with a spacer to prepare a compound represented by the aforementioned formula (I).

Effect of the Invention

According to the present invention, there is provided a fluorescent probe which enables measurement of an substance to be measured in a sample by the ratio method using an excitation wavelength/fluorescence wavelength of the near infrared region, lights of which region show superior biological tissue permeability In the compound represented by aforementioned general formula (I) contained in the fluorescent probe of the present invention, Fluorophore A has a property that it specifically reacts with an substance to be measured to show marked change of the maximum excitation wavelength, and this change originates in change of electron donating ability of the nitrogen atom binding to a methine chain contained in the cyanine fluorophore as Fluorophore A represented by the aforementioned formula (AI), preferably the formula (AII). Accordingly, by variously choosing a group of which ability of the nitrogen atom to donate electron to the cyanine fluorophore is changed by a specific reaction with an substance to be measured, and measuring fluorescence before and after the reaction with the substance to be measured to detect change in efficiency of fluorescence resonance energy transfer between Fluorophore A and Fluorophore B in the aforementioned general formula (I), it becomes possible to measure various objective substances of measurement in deep part tissues in living bodies.

BRIEF DESCRIPTION OF THE DRAWINGS

FIG. 1 shows results of measurement of change in absorption spectrum and fluorescence spectrum of Compound 5 under various pH values. Among the drawings, (A) shows the absorption spectra, (B) shows the fluorescence spectra (excitation wavelength: 640 nm), and (C) shows the fluorescence intensity ratio for 660 nm and 750 nm (excitation wavelength: 640 nm). For all the samples, measurements were performed in a 1:1 mixed solvent of 100 mM sodium phosphate buffered solution and acetonitrile (containing 0.1% or less of DMSO as an auxiliary solvent).

BEST MODE FOR CARRYING OUT THE INVENTION

The fluorescent probe represented by the aforementioned general formula (I) provided by the present invention is used as a fluorescent probe which induces substantial change in efficiency of FRET between Fluorophore A and Fluorophore B before and after a specific reaction with an substance to be measured, and is used as a fluorescent probe for detecting change of the FRET efficiency resulting from contact with the substance to be measured to measure said substance. Type of the substance to be measured is not particularly limited, and examples include hydrogen ion, hydroxyl ion, an enzymatic reaction substrate or enzymatic reaction product, a metal ion (for example, alkali metal ions such as sodium ion and lithium ion, alkaline earth metal ions such as calcium ion, magnesium ion, zinc ion and the like), a nonmetallic ion (carbonate ion and the like), an active oxygen species (for example, nitric oxide, hydroxy radical, singlet oxygen, hydrogen peroxide, peroxynitrite, hypochlorite ion, superoxide, and the like), and the like, but not limited to these examples. Examples of the enzyme involved in the enzymatic reaction include, for example, reductases, oxidases, hydrolases and the like, such as β-lactamase, cytochrome P450 oxidase, β-galactosidase, β-glucosidase, β-glucuronidase, β-hexosaminidase, lactase, and alkaline phosphatase, but not limited to these examples.

In the specification, "FRET" refers to a phenomenon that when two fluorophores exist at positions in a small distance (about 100 Å or shorter) in the molecular of one compound, and a fluorescence spectrum of one of the two fluorophores (donor) and an excitation spectrum of the other (receptor) overlap with each other, irradiation with a light of the excitation wavelength of the donor decreases fluorescence of the donor compared with fluorescence which should be inherently observed, and allows observation of fluorescence of the receptor instead.

In this specification, when the expression "which may have a substituent" is used for a certain functional group, the type, number and substitution position of the substituent are not particularly limited. For example, it may have an alkyl group, an alkoxy group, an aryl group, a halogen atom (it may be any of fluorine atom, chlorine atom, bromine atom, and iodine atom), hydroxy group, amino group, carboxy group or an ester thereof, sulfo group or an ester thereof, or the like as the substituent. In this specification, the aryl group to be used may be any of a monocyclic or polycyclic aryl group, and a monocyclic or polycyclic heteroaryl group, preferably a monocyclic or polycyclic aryl group, and more preferably phenyl group.

In the formula (AI), $R^1$ and $R^2$ independently represent a $C_{1-18}$ alkyl group which may have a substituent. As the alkyl group, a linear, branched, or cyclic alkyl group, or an alkyl group consisting of a combination thereof may be used. For example, a $C_{1-15}$ alkyl group is preferred, a $C_{1-10}$ alkyl group is more preferred, and a $C_{1-6}$ alkyl group is still more preferred. Examples include, for example, methyl group, ethyl group, n-propyl group, isopropyl group, n-butyl group, isobutyl group, sec-butyl group, tert-butyl group, n-pentyl group, isopentyl group, 2-methylbutyl group, 1-methylbutyl group, neopentyl group, 1,2-dimethylpropyl group, 1-ethylpropyl group, n-hexyl group, 4-methylpentyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, 1,3-dimethylbutyl group, 2,3-dimethylbutyl group, 2-ethylbutyl group, 1-ethylbutyl group, 1-ethyl-1-methylpropyl group, n-heptyl group, n-octyl group, n-nonyl group, n-decyl group, n-undecyl group, n-dodecyl group, n-tridecyl group, n-tetradecyl group, n-pentadecyl group, cyclopropyl group, cyclobutyl group, cyclopentyl group, cyclohexyl group, cycloheptyl group, cyclooctyl group, cyclopropylmethyl group, 1-cyclopropylethyl group, 2-cyclopropylethyl group, 3-cyclopropylpropyl group, 4-cyclopropylbutyl group, 5-cyclopropylpentyl group, 6-cyclopropylhexyl group, cyclobutylmethyl group, cyclopentylmethyl group, cyclobutylmethyl group, cyclopentylmethyl group, cyclohexylmethyl group, cyclohexylpropyl group, cyclohexylbutyl group, cycloheptylmethyl group, cyclooctylmethyl group, 6-cyclooctylhexyl group, and the like, but not limited to these. As the alkyl group represented by $R^1$ or $R^2$, a linear alkyl group is preferred.

Examples of the substituent which can exist on the $C_{1-18}$ alkyl group represented by $R^1$ or $R^2$ include, for example, an alkoxy group, an aryl group, a halogen atom (it may be any of fluorine atom, chlorine atom, bromine atom and iodine atom), hydroxy group, amino group, carboxy group or an ester thereof, sulfo group or an ester thereof phospho group or an ester thereof, and the like. Among these, carboxy group, sulfo group and the like are preferred, and they can provide an effect of markedly increasing water-solubility of the compounds of the present invention. Specific example of the alkyl group which has a substituent include, for example, hydroxymethyl group, 1-hydroxyethyl group, 2-hydroxyethyl group, 2-hydroxypropyl group, 3-hydroxypropyl group, 4-hydroxybutyl group, carboxymethyl group, sulfomethyl group, 2-sulfoethyl group, 3-sulfopropyl group, 4-sulfobutyl group, and the like. Both $R^1$ and $R^2$ may be unsubstituted $C_{1-18}$ alkyl groups, or one of these $C_{1-18}$ alkyl groups may have a substituent. $R^1$ and $R^2$ preferably represent a linear $C_{1-6}$ alkyl group or a $C_{1-6}$ alkyl group substituted with sulfo group, particularly preferably methyl group. The above explanations for $R^1$ and $R^2$ in the aforementioned formula (AI) are similarly applied to $R^{11}$ and $R^{12}$ in the general formula (AII).

In the formula (AI), $R^3$ and $R^4$ independently represent hydrogen atom, or the substituent for detecting an substance to be measured explained above. However, $R^3$ and $R^4$ do not simultaneously represent hydrogen atom, and $R^3$ and $R^4$ may bind to each other to form a ring structure for detecting an substance to be measured. In this specification, the term "detection of an substance to be measured" includes, besides detection by conversion of a functional group by a chemical reaction with an substance to be measured, detection by capture of ion or the like. In this specification, the term "capture" should be construed in its broadest sense, including capture by chelation of a metal ion or the like without substantial chemical change of $R^3$ and/or $R^4$, as well as change of chemical structure of $R^3$ and/or $R^4$ caused by a chemical reaction with an substance to be measured, and should not be construed in any limitative way.

As the substituent for capturing an substance to be measured, various substituents have been proposed, and those skilled in the art can appropriately choose it according to type of the substance to be measured. For example, International Patent Publication WO01/062755, Japanese Patent Laid-open Publication No. 2004-315501 and the like can be referred to. Further, the substituents for capturing an substance to be measured described in the catalogue of Molecular Probe (Handbook of Fluorescent Probes and Research Chemicals, Tenth Edition), Chapter 19 (Calcium ion, magnesium ion, zinc ion and other metal ions), Chapter 20 (pH indicators), and Chapter 21 (Sodium ion, potassium ion, chlorine ion and other inorganic ions) can also be used. However, the substituent for capturing an substance to be measured is not limited to those described in the aforementioned publications. As the substituent for detection of an enzymatic reaction substrate or an enzymatic reaction product, when sugar hydrolase activity is measured, for example, a residue of a sugar compound used as the substrate of the enzyme can be used as $R^3$ or $R^4$. Functional groups contained in the sugar compound such as hydroxy group and amino group may be protected with appropriate protective groups, if needed. All the compounds having such protective groups also fall within the scope of the present invention.

For example, in the fluorescent probe for measurement of pH, one of $R^3$ and $R^4$ may be hydrogen atom, and the other may be a $C_{1-18}$ alkyl group which may have a substituent, preferably a $C_{1-6}$ alkyl group which may have a substituent. As the alkyl group, a linear alkyl group is preferred. Examples of the substituent which can exist on the $C_{1-18}$ alkyl group which may have a substituent include, for example, an alkoxy group, an aryl group, a halogen atom (the halogen may be any of fluorine atom, chlorine atom, bromine atom and iodine atom), hydroxy group, amino group, carboxy group or an ester thereof, sulfo group or an ester thereof phospho group or an ester thereof, and the like. The $C_{1-6}$ alkyl group which may have a substituent is preferably a carboxy-substituted $C_{1-6}$ alkyl group, particularly preferably 5-carboxypentyl group.

Further, in the fluorescent probe used for pH measurement, it is preferred that $R^3$ and $R^4$ independently represent a $C_{1-18}$ alkyl group which may have a substituent, an aryl group which may have a substituent, or $—(CH_2)_m—N(R^{21})(R^{22})$, and one of $R^3$ and $R^4$ is $—(CH_2)_m—N(R^{21})(R^{22})$ ($R^{21}$ and $R^{22}$ independently represent a $C_{1-6}$ alkyl group which may have a substituent, or an aryl group which may have a substituent, or $R^{21}$ or $R^{22}$ binds to $R^3$ or $R^4$, to represent ethylene, and m represents 1 or 2). As the $C_{1-18}$ alkyl group which may have a substituent represented by $R^3$ or $R^4$, a $C_{1-6}$ alkyl group which may have a substituent is preferred, and it is especially preferred that it is methyl group. Examples of the substituent which can exist on the $C_{1-18}$ alkyl group include, for example, an alkoxy group, an aryl group, a halogen atom (the halogen may be any of fluorine atom, chlorine atom, bromine atom and iodine atom), hydroxy group, amino group, carboxy group or an ester thereof, sulfo group or an ester thereof, and the like. As the $C_{1-18}$ alkyl group which may have a substituent represented by $R^{21}$ or $R^{22}$, a $C_{1-6}$ alkyl group which may have a substituent is preferred, and methyl group, ethyl group, or benzyl group is especially preferred. It is also preferred that $R^{21}$ or $R^{22}$ binds to $R^3$ or $R^4$, to form a $C_{1-3}$ alkylene group. Further, the alkylene group may have a substituent such as an alkoxy group, an aryl group, a halogen atom (it may be any of fluorine atom, chlorine atom, bromine atom, and iodine atom), hydroxy group, amino group, carboxy group or an ester thereof, and sulfo group or an ester thereof, and it is particularly preferably ethylene group. Preferably m is 2. The above explanations for $R^3$ and $R^4$ in the aforementioned formula (AI) are similarly applied to $R^{13}$ and $R^{14}$ in the formula (AII).

As for the substituents mentioned above, it is preferred that Fluorophore A is a group represented by the formula (AI), and
(1) $R^3$ is methyl group, $R^4$ is a group represented by —$(CH_2)_m$—$N(R^{21})(R^{22})$, $R^{21}$ and $R^{22}$ are methyl groups, and m is 2;
(2) $R^3$ is methyl group, $R^4$ is a group represented by —$(CH_2)_m$—$N(R^{21})(R^{22})$, $R^{21}$ and $R^{22}$ are ethyl groups, and m is 2;
(3) $R^3$ is a group represented by —$(CH_2)_m$—$N(R^{21})(R^{22})$, m is 2, $R^{21}$ is benzyl group, and $R^4$ binds to $R^{22}$ to form ethylene group;
(4) $R^3$ is a group represented by —$(CH_2)_m$—$N(R^{21})(R^{22})$, m is 2, $R^{21}$ is methyl group, and $R^4$ binds to $R^{22}$ to form ethylene group; or
(5) $R^3$ is a group represented by —$(CH_2)_m$—$N(R^{21})(R^{22})$, m is 2, $R^{21}$ is phenyl group, and $R^4$ binds to $R^{22}$ to form ethylene group.

Furthermore, for example, in the fluorescent probe for measurement of zinc ion, it is preferred that $R^3$ and $R^4$ independently represent hydrogen atom, or a group represented by the aforementioned formula (D) (wherein $W^1$, $W^2$, $W^3$ and $W^4$ independently represent hydrogen atom, 2-pyridylmethyl group, 2-pyridylethyl group, 2-methyl-6-pyridylmethyl group, or 2-methyl-6-pyridylethyl group, provided that at least one of groups selected from the group consisting of $W^1$, $W^2$, $W^3$ and $W^4$ represents 2-pyridylmethyl group, 2-pyridylethyl group, 2-methyl-6-pyridylmethyl group, and 2-methyl-6-pyridylethyl group; and p and q independently represent 0 or 1). However, $R^3$ and $R^4$ do not simultaneously represent hydrogen atom. In this case, it is preferred that p is 0, q is 1, $W^4$ is hydrogen atom, and at least one of $W^1$ and $W^2$ is a group selected from the group consisting of 2-pyridylmethyl group, 2-pyridylethyl group, 2-methyl-6-pyridylmethyl group and 2-methyl-6-pyridylethyl group, and it is particularly preferred that both $W^1$ and $W^2$ are 2-pyridylmethyl groups. Furthermore, it is also preferred that p is 0, q is 0, and at least one of $W^1$ and $W^2$ is a group selected from the group consisting of 2-pyridylmethyl group, 2-pyridylethyl group, 2-methyl-6-pyridylmethyl group, and 2-methyl-6-pyridylethyl group.

In the formula (AI), $R^1$ to $R^4$ may be independently a group which can be buried in a cell membrane. In the aforementioned case, the compounds of the present invention represented by general formula (I) can be used as a membrane localized type fluorescent probe to measure pH change only around cell membranes. As the group which can be buried in a cell membrane, a group consisting of a $C_{1-18}$ alkyl group which may have a substituent as any one of $R^1$ to $R^4$ in the general formula (I) to which a linear or branched $C_{7-18}$ alkyl group and a phospholipid (for example, phosphatidylethanolamines, phosphatidylcholines, phosphatidylserines, phosphatidylinositols, phosphatidylglycerols, cardiolipins, sphingomyelins, ceramide phosphorylethanolamines, ceramide phosphorylglycerols, ceramide phosphorylglycerol phosphates, 1,2-dimyristoyl-1,2-deoxyphosphatidylcholines, plasmalogens, and phosphatidic acids can be exemplified, but the aliphatic acid residue in these phospholipids is not particularly limited, and phospholipids having one or two saturated or unsaturated aliphatic acid residues having about 12 to 20 carbon atoms can be used) are bound via the substituent, and the like are preferred.

$Y^1$ and $Y^2$ independently represent —O—, —S—, —Se—, —CH=CH—, —$C(R^5)(R^6)$—, or —$N(R^7)$—, and $R^5$, $R^6$, and $R^7$ independently represent hydrogen atom or a $C_{1-6}$ alkyl group which may have a substituent. $Y^1$ and $Y^2$ are preferably —$C(R^5)(R^6)$—, and $R^5$ and $R^6$ are preferably methyl groups. The above explanations about $Y^1$ and $Y^2$ in the aforementioned formula (AI) are similarly applied to $Y^{11}$ and $Y^{12}$ in the formula (AII).

In the general formula (AI), $Z^1$ and $Z^2$ independently represent a nonmetallic atom group required to form a benzo-condensed ring which may have a substituent or a naphtho-condensed ring which may have a substituent. More specifically, for example, $Z^1$ and $Z^2$ each form any of the following benzo-condensed ring and naphtho-condensed rings. The benzo-condensed ring and the naphtho-condensed ring may have a substituent such as an alkoxy group, an aryl group, a halogen atom (it may be any of fluorine atom, chlorine atom, bromine atom, and iodine atom), hydroxy group, amino group, carboxy group or an ester thereof and sulfa group or an ester thereof. The above explanations for $Z^1$ and $Z^2$ in the aforementioned formula (AI) are also similarly applied to $Z^{11}$ and $Z^{12}$ in the formula (AII).

[Formula 5]

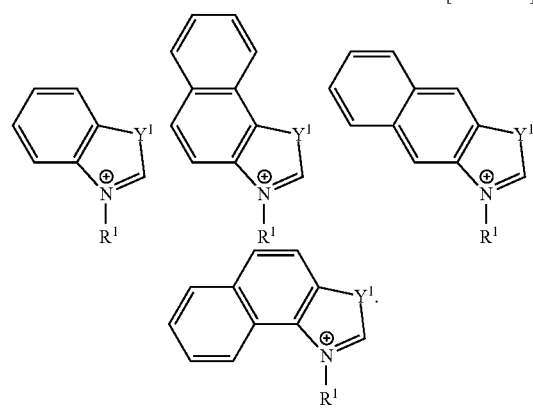

In the formula (AI), it is preferred that the sum of n and n' is 2, and it is particularly preferred that both n and n' are 1. The fluorophore represented by the formula (AI) preferably shows a maximum absorption wavelength in the region of 400 to 1300 nm, more preferably 650 to 950 nm, still more preferably 650 to 800 nm. Those skilled in the art would understand that as n or n' in the fluorophore represented by the formula (AI) in the compounds of the present invention represented by the aforementioned general formula (I) increases, the excitation wavelength and fluorescence wavelength thereof become larger, and in the same manner, as n or n' decreases, the excitation wavelength and fluorescence wavelength become smaller.

$L^1$, $L^2$, $L^3$, $L^4$, $L^5$, $L^6$ and $L^7$ independently represent a substituted or unsubstituted methine group, and they may be the same or different. Further, when n is 2, two each of $L^1$ and $L^2$ may be the same or different, and when n' is 2, two each of $L^6$ and $L^7$ may be the same or different. Substituents of the methine groups represented by $L^1$, $L^2$, $L^3$, $L^4$, $L^5$, $L^6$ and $L^7$ may bind to each other to form a ring containing three contiguous methine groups, and this ring may form a condensed ring with a ring containing other methine groups. As the partial structure constituted by $L^1$, $L^2$, $L^3$, $L^4$, $L^5$, $L^6$ and $L^7$, the structures mentioned below are particularly preferred.

[Formula 6]

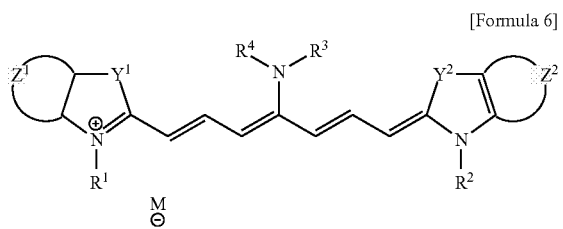

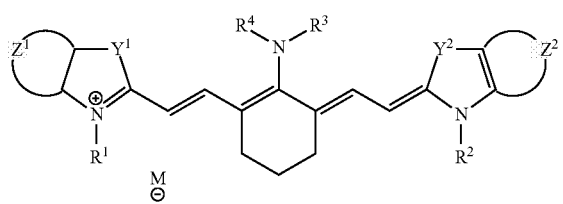

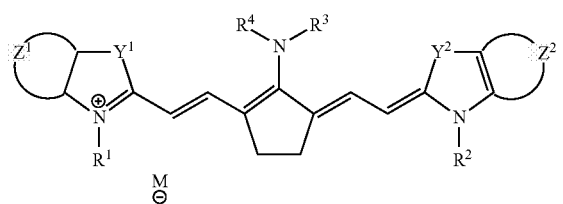

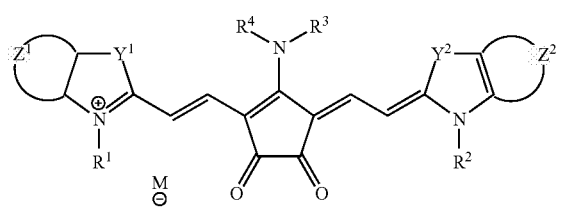

Fluorophore B is not particularly limited, and an arbitrary fluorophore can be chosen, so far that a fluorophore serving as a donor or receptor is chosen which can induce fluorescence resonance energy transfer with Fluorophores A represented by the formula (AI). For example, when the sum of n and n' is 2 in the formula (AI), Fluorophore A has the maximum excitation wavelength of about 650 to 800 nm, and therefore a fluorophore showing a fluorescence wavelength in this excitation light region, for example, a cyanine fluorophore comprising a tetramethylindodicarbocyanine derivative, a rhodamine derivative, or the like may be appropriately chosen as Fluorophore B. In the aforementioned case, by irradiating Fluorophore B (when Fluorophore B is a donor) with an excitation light, and measuring fluorescence emitted by Fluorophore A and Fluorophore B, efficiency change of FRET to Fluorophore A can be detected.

Length of the spacer represented by S can be suitably chosen in such a range that FRET should be induced between Fluorophore A and Fluorophore B. As the spacer, an alkyl group which may have a substituent represented by any one of $R^1$ to $R^4$ in Fluorophore A represented by the formula (AI) in the general formula (I) may be used, or an alkyl chain, a polyethylene glycol chain, a polyamino acid or the like may be introduced by using a substituent of the alkyl group which may have a substituent represented by any one of $R^1$ to $R^4$. Further, the spacer preferably contains a structurally rigid group such as cyclohexane. In the aforementioned case, degree of freedom of the compounds represented by general formula (I) is decreased, thus fluorophores of the donor and the receptor hardly associate with each other, and an effect of preventing formation of non-fluorescent aggregates may be obtained.

$M^-$ represents a counter ion in a number required for neutralizing electrical charge. Examples of the counter ion include, metal ions such as sodium ion, potassium ion and magnesium ion, quaternary ammoniums, halogen ions such as iodine ion, ions of amino acids such as glycine. For example, when carboxy group, sulfo group, or the like exists on the $C_{1-18}$ alkyl group represented by $R^1$ or $R^2$ in Fluorophore A represented by the formula (AI) in the general formula (I), or one or more of $R^3$, $R^4$, $R^5$, $R^6$, $R^7$, $Z^1$, and $Z^2$ contain carboxy group, sulfo group, phospho group or the like, two or more counter ions may be needed as $M^-$. Further, when one carboxy group or sulfo group exists in the $C_{1-18}$ alkyl group represented by one of $R^1$ and $R^2$ in Fluorophore A represented by the formula (AI) in the general formula (I), there may be a case that the positive charge of the quaternary nitrogen atom to which $R^1$ binds and the anion of carboxy group or sulfo group form an intramolecular zwitterion, and therefore the counter ion required for neutralization of electrical charge is unnecessary.

The compounds of the present invention represented by the aforementioned general formula (1) may have one or more asymmetric carbons. Therefore, any of arbitrary optical isomers in an optically pure form, arbitrary mixtures of optical isomers, racemates, diastereoisomers in a pure form, mixtures of diastereoisomers, and the like based on one or more asymmetric carbon atoms fall within the scope of the present invention. The compounds of the present invention may exist as a hydrate or solvate, and these substances of course also fall within the scope of the present invention.

In the aforementioned general formula (I), it is preferred that Fluorophore A is a fluorophore represented by the formula (AI) (wherein $R^1$ and $R^2$ represent methyl group and 4-sulfobutyl group, $Y^1$ and $Y^2$ represent —$C(CH_3)_2$—, both n and n' represent 1, $Z^{11}$ and $Z^{12}$ represent an unsubstituted benzo-condensed ring, and $L^1$, $L^2$, $L^3$, $L^4$, $L^5$, $L^6$ and $L^7$ represent an unsubstituted methine group), and Fluorophore B is a tetramethylindodicarbocyanine derivative. An example of the fluorescent probe for measurement of pH includes the following compound as an especially preferred compound among the compounds represented by the general formula (I), but the probe is not limited to this specific compound.

[Formula 7]

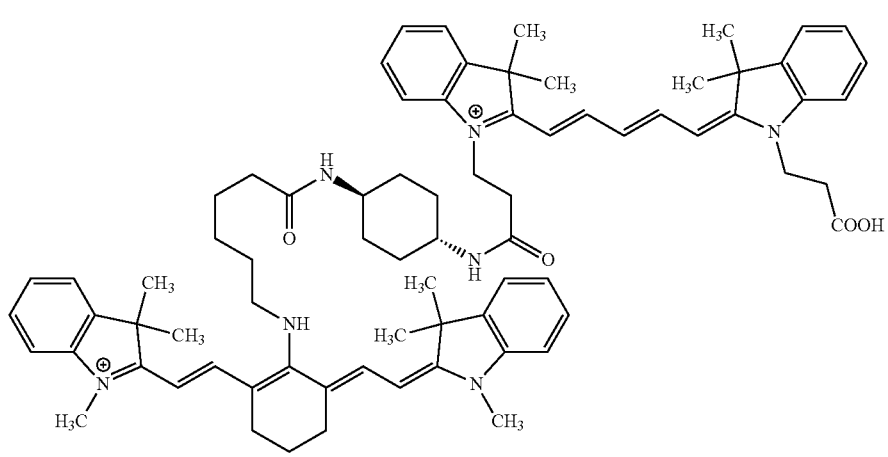

The compounds represented by the aforementioned general formula (I) can be prepared by, for example, the method shown in the following scheme. Further, preparation methods of typical compounds included in the compounds represented by the aforementioned general formula (I) are specifically shown in Examples of this specification. It should be understood by those skilled in the art that the compounds represented by the aforementioned general formula (I) can be readily prepared by referring to the following scheme and the specific explanations in Examples.

[Formula 8]

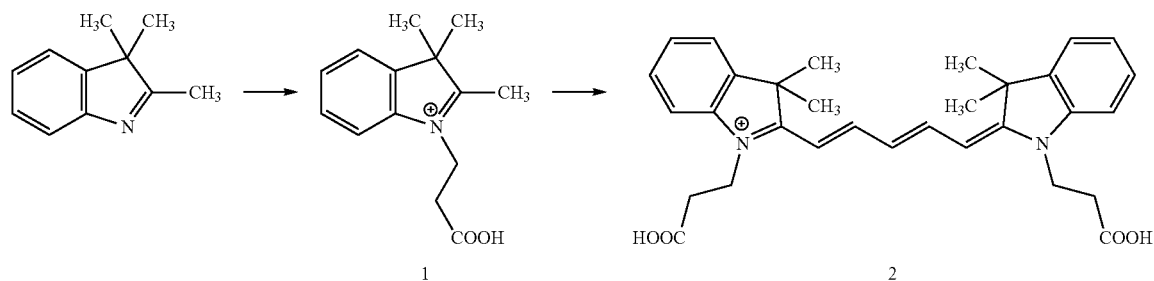

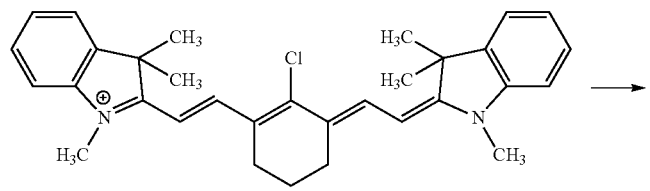

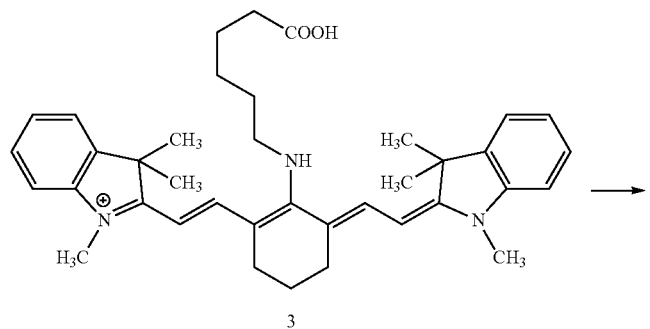

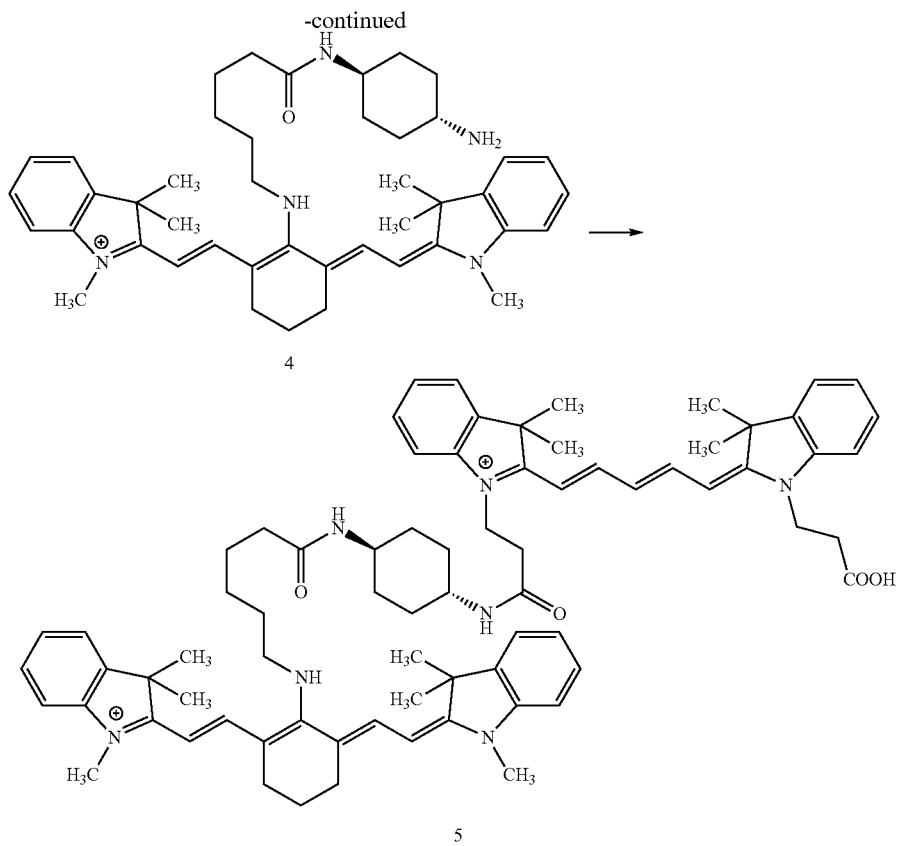

The compounds represented by the aforementioned general formula (I) have a property that they emit strong fluorescence with an excitation light of the near infrared region around 650 to 950 nm, which shows superior permeability for biological tissues, and Fluorophore A represented by the formula (AI) has properties: (a) it reacts with an substance to be measured at a substituent binding to a methine chain such as $L^1$ to show change of electron donating ability; (b) it shows marked wavelength shift in the peak of excitation spectrum according to the change of electron donating ability of the nitrogen atom directly binding to the cyanine fluorophore; and (c) it shows substantial change in efficiency of FRET with Fluorophores B in association with the wavelength shift of the peak of excitation spectrum. In the case of Compound 5, for example, the tricarbocyanine fluorophore is a pH-sensitive FRET receptor, the dicarbocyanine fluorophore is an FRET donor, and the compound has a property that when the nitrogen atom binding to the methine chain of the tricarbocyanine fluorophore is protonated, the peak in the excitation spectrum shifts from around 660 nm to the longer wavelength side in connection with decrease of electron donating ability. On the basis of this property, when the compound is irradiated with a light of the excitation wavelength of the dicarbocyanine fluorophore (when the compound is irradiated with an excitation light of 640 nm, it emits fluorescence with a fluorescence wavelength peak of around 660 nm), (1) where the nitrogen atom is not protonated, FRET from the dicarbocyanine fluorophore to the tricarbocyanine fluorophore is efficiently induced, and strong fluorescence from the tricarbocyanine fluorophore (wavelength of around 750 nm) is observed, and (2) where the nitrogen atom is protonated, FRET from the dicarbocyanine fluorophore to the tricarbocyanine fluorophore is not efficiently induced, and strong fluorescence from the dicarbocyanine fluorophore (wavelength of around 660 nm) is observed. Namely, by dissolving Compound 5 in a test sample, performing excitation with a light of 640 nm, and measuring ratio of fluorescence intensities at 660 nm and 750 nm upon excitation, it becomes possible to detect pH by the ratio method. Compound 5 is especially useful as a pH fluorescent probe for measuring pH in live cells or live tissues, in particular, in deep part tissues, under a physiological condition.

The details of the ratio method mentioned in this specification are described in the book by Mason W. T. (Mason W. T. in Fluorescent and Luminescent Probes for Biological Activity, Second Edition, Edited by Mason W. T., Academic Press), and the like, and specific examples of the measurement method using the compounds of the present invention are also shown in Examples of the specification. The term "measurement" used in the specification should be construed in its broadest sense, including quantitative and qualitative measurements. Further, the term "detection" used in this specification includes, for example, a concept of calculating a result by using measured values, for example, a concept of calculating change of FRET efficiency.

The method for using the fluorescent probe of the present invention is not particularly limited, and the probe can be used in the same manner as conventionally known fluorescent probes. In general, a substance selected from the compounds represented by the aforementioned general formula (I) and salts thereof is dissolved in an aqueous medium such as physiological saline or a buffered solution, or in a mixture of an aqueous medium and a water-miscible organic solvent such as ethanol, acetone, ethylene glycol, dimethyl sulfoxide, and dimethylformamide, then the resultant solution is added to a suitable buffered solution containing cells or tissues, and (1) two-wavelength excitation/one-wavelength fluorescence measuring type ratio measurement can be performed, in which excitation is attained with appropriately selected two different wavelengths of the near infrared region around 650 to 950 nm, which show superior permeability for biological tissues, and fluorescence intensities can be measured for each excitation, or (2) one-wavelength excitation/two-wavelength fluorescence type ratio measurement can be performed, in which excitation is attained at one kind of wavelength of the near infrared region around 650 to 950 nm, which show superior permeability for biological tissues, and fluorescence intensity is measured at appropriately selected two different wavelengths. The pH fluorescent probe of the present invention may be combined with an appropriate additive and used in the form of a composition. For example, it may optionally be combined with additives such as buffers, and dissolving aids.

EXAMPLES

Hereafter, the present invention will be more specifically explained with reference to examples. However, the scope of the present invention is not limited to the following examples (the compound numbers used in the following examples correspond to the compound numbers used in the aforementioned scheme).

Example 1

Synthesis of Compound 5

(A) Synthesis of Compound 1

2,3,3-Trimethyl-3H-indole (7.2 g, 45 mmol) and 3-iodopropionic acid (13 g, 63 mmol) were dissolved in o-dichlorobenzene. The solution was heated and stirred at 110° C. for 15 hours under an argon atmosphere. The precipitates obtained by filtration were washed with diethyl ether and acetone to obtain Compound 1 (11 g).

(B) Synthesis of Compound 2

Malonaldehyde disnilide monohydrochioride (0.68 g, 2.6 mmol) and diisopropylethylamine (0.69 g, 5.3 mmol) were suspended to dichloromethane (6 mL). A mixed solution of acetic anhydride (0.36 g, 3.5 mmol) and dichloromethane (6 mL) was added dropwise to the suspension under ice cooling, and the mixture was further stirred for 1 hour under ice cooling (yellow reaction mixture). Separately, Compound 1 and sodium acetate (0.85 g, 10 mmol) were dissolved in,a mixed solution of acetonitrile (25 mL) and water (1 mL), and refluxed, and the previously obtained yellow reaction mixture was added dropwise to this solution. After this solution was refluxed for 1 hour, then was left to cool to room temperature. The precipitates were collected by filtration, and washed with acetonitrile, 5% aqueous hydrochloric acid and diethyl ether to obtain Compound 2 (0.68 g).

(C) Synthesis of Compound 3

IR-786 (Sigma, 0.50 g, 0.86 mmol) and 6-amino-n-caproic acid (0.46 g, 3.5 mmol) were dissolved in dimethylformamide (DMF, 30 mL), and the solution was heated at 80° C. for 3 hours under an argon atmosphere. After the reaction mixture was left to cool to room temperature, the solvent was evaporated under reduced pressure. The residue was purified by column chromatography using NH silica gel to obtain Compound 3 (0.42 g).

(D) Synthesis of Compound 4 trans-1,4-Cyclohexanediamine (0.19 g, 1.7 mmol) was dissolved in DMF (20 mL). A solution of Compound 3 (0.42 g, 0.61 mmol), 1-hydroxybenzotriazole monohydrate (HOBT.H$_2$O, 0.19 g, 1.3 mmol), O-(benzotriazol-1-yl)-N,N,N',N'-tetramethyluronium hexafluorophosphate (HBTU, 0.47 g, 1.2 mmol), and diisopropylethylamine (85 mg, 0.66 mmol) in DMF (40 mL) was added dropwise to this solution at room temperature with stirring. After the mixture was stirred at room temperature for 3 hours under an argon atmosphere, the solvent was evaporated under reduced pressure. The residue was purified by column chromatography using NH silica gel to obtain Compound 4 (0.35 g).

(E) Synthesis of Compound 5

Compound 4 (0.15 g, 0.21 mmol) was dissolved in DMF (20 mL). This solution was added dropwise to a solution of Compound 2 (0.25 g, 0.40 mmol), HOBT.H$_2$O (94 mg, 0.61 mmol), HBTU (0.24 g, 0.62 mmol), and diisopropylethylamine (85 mg, 0.66 mmol) in DMF (20 mL) at room temperature with stirring. After the mixture was stirred at room temperature for 3 hours under an argon atmosphere, the solvent was evaporated under reduced pressure. The residue was purified by column chromatography using NH silica gel to obtain Compound 5 (35 mg).

$^1$H-NMR (300 MHz, CD$_3$OD): δ 0.98-1.94 (m, 40H), 2.03 (t, 2H, J=8.0 Hz), 2.41-2.52 (m, 8H), 3.32 (s, 6H), 3.40 (br, 2H), 3.63 (t, 2H, J=6.8 Hz), 4.25 (br, 4H), 5.65 (d, 2H, J=13.0 Hz), 6.15, (d, 1H, J=13.3 Hz), 6.33 (d, 1H, J=13.3 Hz), 6.51 (t, 1H, J=13.3 Hz), 6.94-7.36 (m, 16H), 7.63 (d, 2H, J=13.0 Hz), 8.11 (tt, 2H, J=13.2 Hz, 13.2 Hz)

HRMS (ESI$^+$) Calcd for [M−H]$^+$, 1154.7211, Found, 1154.7243

Example 2

Spectral Change of Compound 5 in Association with pH Change

In a 1:1 mixed solution of 100 mmol/L phosphate buffer (pH 1.2, 2.1, 3.3, 3.9, 5.0, 6.0, 6.8) and acetonitrile (containing 0.1% or less of DMSO as an auxiliary solvent), absorption spectra and fluorescence spectra (excitation wavelength: 640 nm) of Compound 5 were measured. The absorption spectra are shown in FIG. 1, (A), and the fluorescence spectra are shown in FIG. 1, (B). It can be understood that with elevation of pH, the absorbance around 650 nm increased, and the absorption spectrum changed. Moreover, it can also be understood that in the fluorescence spectrum, with elevation of pH, the fluorescence intensity decreased around 660 nm, and increased around 750 nm. Therefore, pH change can be accurately measured by using the ratio method based on one-wavelength excitation/ two-wavelength fluorescence measurement. FIG. 1(C) shows ratio of fluorescence intensities at 660 nm and 750 nm. The fluorescence intensities at 660 nm and 750 nm linearly change from pH 4 to 6, and accordingly, pH of this range can be measured by using Compound 5.

Industrial Applicability

By using the fluorescent probe provided by the present invention, an substance to be measured in a sample can be measured by the ratio method using excitation wavelength/ fluorescence wavelength of the near infrared region, wavelengths of which show superior biological tissue permeability.

What is claimed is:

1. A fluorescent probe comprising a compound represented by the following general formula (I):

(Fluorophore A)-S-(Fluorophore B)  (I)

wherein Fluorophore A and Fluorophore B are fluorophores which emit fluorescence when they are irradiated with an excitation light of a wavelength of 600 to 950 nm, Fluorophore A has a property that it shows change of fluorescence characteristic before and after a specific reaction with a substance to be measured, and S represents a spacer which connects Fluorophore A and Fluorophore B, which compound shows substantial change in efficiency of fluorescence resonance energy transfer between Fluorophore A and Fluorophore B before and after the specific reaction with the substance to be measured, wherein Fluorophore A is represented by the following formula (AI):

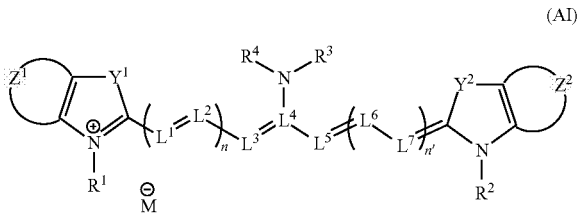

(AI)

wherein $R^1$ and $R^2$ independently represent a $C_{1-18}$ alkyl group which may have a substituent; $R^3$ and $R^4$ independently represent hydrogen atom, or a substituent for detecting the substance to be measured, provided that $R^3$ and $R^4$ do not simultaneously represent hydrogen atom, and $R^3$ and $R^4$ may bind to each other to form a ring structure for detecting the substance to be measured; $Y^1$ and $Y^2$ independently represent —O—, —S—, —Se—, —CH=CH—, —C($R^5$)($R^6$)—, or —N($R^7$)— (wherein $R^5$, $R^6$ and $R^7$ independently represent hydrogen atom, or a $C_{1-6}$ alkyl group which may have a substituent); n and n' independently represent 0, 1 or 2; $Z^1$ and $Z^2$ independently represent a nonmetallic atom group required to form a benzo-condensed ring which may have a substituent or a naphtho-condensed ring which may have a substituent; $L^1$, $L^2$, $L^3$, $L^5$, $L^6$ and $L^7$ independently represent a substituted or unsubstituted methine group, $L^4$ represents a substituted methine group, provided that when n or n' is 2, each two of $L^1$ and $L^2$, or each two of $L^6$ and $L^7$ may be the same or different; $M^-$represents a counter ion in a number required for neutralizing electrical charge, and the combination of $R^3$ and $R^4$ is a combination that provides change in the maximum excitation wavelength of Fluorophore A represented by the formula (AI) before and after detection of the substance to be measured;

Fluorophore B is a tetramethylindodicarbocyanine derivative; and

S is a spacer of a length so that FRET is induced between Fluorophore A and Fluorophore B.

2. The fluorescent probe according to claim 1, wherein the substance to be measured is a proton, a metal ion, an active oxygen species, an enzymatic reaction substrate, or an enzymatic reaction product.

3. The fluorescent probe according to claim 1, wherein the fluorescent probe is used for pH measurement, and Fluorophore A is represented by the formula (AI), wherein $R^1$ and $R^2$ independently represent methyl group or 4-sulfobutyl group; one of $R^3$ and $R^4$ is hydrogen atom, and the other is a $C_{1-18}$ alkyl which may have a substituent; $Y^1$ and $Y^2$ represent —C(CH$_3$)$_2$—; both n and n' represent 1; both $Z^1$ and $Z^2$ represent an unsubstituted benzo-condensed ring; $L^1$, $L^2$, $L^3$, $L^5$, $L^6$ and $L^7$ represent unsubstituted methine group; and $M^-$represents a counter ion in a number required for neutralizing electrical charge.

4. The fluorescent probe according to claim 1, wherein the fluorescent probe is used for pH measurement, and Fluorophore A is represented by the formula (AI), wherein $R^1$ and $R^2$ independently represent methyl group or 4-sulfobutyl group; $R^3$ and $R^4$ independently represent a $C_{1-18}$ alkyl group which may have a substituent, an aryl group which may have a substituent, or —(CH$_2$)$_m$—N($R^{21}$)($R^{22}$), one of $R^3$ or $R^4$ is —(CH$_2$)$_m$—N($R^{21}$)($R^{22}$) ($R^{21}$ and $R^{22}$ independently represent a $C_{1-6}$ alkyl group which may have a substituent, or an aryl group which may have a substituent, or $R^{21}$ or $R^{22}$ binds to $R^3$ or $R^4$, respectively, to represent a $C_{1-3}$ alkylene group which may have a substituent, and m represents 1 or 2); $Y^1$ and $Y^2$ represent —C(CH$_3$)$_2$—; both n and n' represent 1, $Z^1$ and $Z^2$ represent an unsubstituted benzo-condensed ring, and $L^1$, $L^2$, $L^3$, $L^5$, $L^6$ and $L^7$ represent unsubstituted methine group; and $M^-$represents a counter ion in a number required for neutralizing electrical charge.

5. The fluorescent probe according to claim 1, which is a fluorescent probe for pH measurement and contains the following compound;

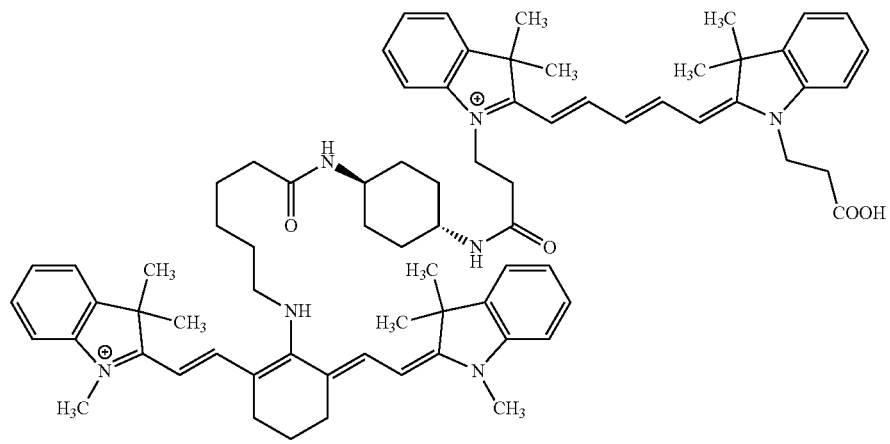 [SMILES: CN1/C(=C/C=C2\CCCC(/C=C/C3=[N+](C)c4ccccc4C3(C)C)=C2NCCCCCC(=O)N[C@H]2CC[C@H](NC(=O)CC[N+]3=C(/C=C/C=C/C=C4/N(CCC(=O)O)c5ccccc5C4(C)C)C(C)(C)c4ccccc43)CC2)C(C)(C)c2ccccc21]

6. A method for fluorometry of a substance to be measured, which comprises (a) contacting a compound represented by the general formula (I) according to claim 1 and a substance to be measured, and (b) measuring fluorescence intensity of the compound represented by the general formula (I) after the contacting of (a) to detect change of FRET efficiency originating in the contacting with the substance to be measured.

7. A method for fluorometry of a substance to be measured, which comprises (a) contacting the compound according to claim 5 and a substance to be measured, and (b) measuring fluorescence intensity of the compound after the contacting of (a) to detect change of FRET efficiency originating in the contacting with the substance to be measured.

* * * * *